United States Patent [19]

Riede et al.

[11] Patent Number: 5,284,651
[45] Date of Patent: Feb. 8, 1994

[54] HUMINATES, PROCESS AND USES

[75] Inventors: Urs N. Riede, Freiburg; Bernhard Seubert, Edingen, both of Fed. Rep. of Germany

[73] Assignee: Rutgerswerke Aktiengesellschaft AG, Fed. Rep. of Germany

[21] Appl. No.: 960,898

[22] Filed: Oct. 14, 1992

[30] Foreign Application Priority Data

Oct. 17, 1991 [DE] Fed. Rep. of Germany ....... 4134379

[51] Int. Cl.$^5$ .................... A61K 31/74; C08G 65/38; C07G 17/00
[52] U.S. Cl. .................... 424/78.06; 528/212; 528/219; 522/47; 522/181
[58] Field of Search .............. 424/78.06; 514/734, 514/730; 522/47, 181; 528/212, 219

[56] References Cited

U.S. PATENT DOCUMENTS 4,921,840  5/1990  Seubert et al. ................ 514/33
4,942,181  7/1990  Riede et al. ................... 514/730

OTHER PUBLICATIONS

Chem. Ab. vol. 104: 6219r.
Chimika Chronika New Series, 1, 203–209 (1972).
Chem. Ab. vol. 103: 98707d.
Chem. Ab. vol. 105: 96590c.

*Primary Examiner*—Thurman K. Page
*Assistant Examiner*—Peter F. Kulkosky
*Attorney, Agent, or Firm*—Bierman and Muserlian

[57] ABSTRACT

Physiologically active, non-toxic, non-teratogenic and non-mutagenic huminates produced by oxidation of polyvalent phenols in aqueous alkaline medium at a reaction temperature under 40° C., the pH value of the reaction medium always being over 9.0 during the oxidation and the supply of oxidant being proportioned so that the content of the quinones corresponding to the polyvalent phenols is always less than 0.5%, based on the polyvalent phenols used, and that the oxidation reaction is stopped when the quinone concentration decreases despite oxidant supply.

5 Claims, No Drawings

HUMINATES, PROCESS AND USES

STATE OF THE ART

U.S. Pat. No. 4,914,059 describes alkali metal and ammonium salts of humic acids of low molecular weight as having a wound healing action, and that the said huminates, in contrast to humins previously known, or respectively their salts, are much less toxic. These low-molecular weight humins can either be isolated from naturally occurring humins or produced synthetically as taught in U.S. Pat. No. 4,921,840 in which polyvalent phenols are oxidized in alkaline solution with the pH of the reaction mixture of 8.8 to 9.0. This reaction condition ensures that only low-molecular weight huminates are formed whose mean molecular weight is about 1000 with a range of 300 to 1500. Only these huminates are regarded to be physiologically active but non-toxic, non-mutagenic and non-teratogenic.

Adjusting and maintaining a pH value in the narrow range of 8.8 to 9.0 and the pH value in the range of 6.2 to 7.2 to be adjusted during processing are unfavorable inasmuch as the buffer capacity of aqueous solutions is extremely low in the range from pH 6.0 to 9.0, so that due to small changes in the concentration of acid or base, pH values of the reaction medium occur which lie outside the specified range.

OBJECTS OF THE INVENTION

It is an object of the invention to provide a simple and easy-to-control process for the preparation of physiologically active, non-toxic, non-mutagenic huminates and the huminates produced thereby.

It is another object of the invention to provide novel methods of treating various conditions.

These and other objects and advantages of the invention will become obvious from the following detailed description.

THE INVENTION

The novel process of the invention for the production of physiologically active, non-toxic, non-teratogenic and non-mutagenic huminates comprises oxidizing polyvalent phenols in an aqueous alkaline medium at a pH greater than 9.0 and at a temperature less than 40° C. while regulating the oxidant to maintain the amount of quinones to less than 0.5% based on the polyvalent phenols, stopping the oxidation when the quinon concentration begins to decrease and recovering the huminate.

Contrary to the prior art belief, the desired physiological properties of a medicament with low toxicity and non-mutagenicity

Result

In basin a, a mortality rate of 16% (Guppy) or respectively 50% (red phantom salmon fish) and a generally poor vitality of the fish was observed. In basin b, the mortality had fallen to 10.5% and 19%, respectively, and the vitality of the surviving fish was moderate. In basin c, the mortality was 5% and by and large, the vitality was good.

Detoxification of water

The toxicity of the huminate produced in the example was determined by Daphnia magna (test according to OECD guidelines). The $LC_{50}$ designated the concentration of a substance in water which after the stated time was lethal in 50% of the tested animals. The $LC_{50}$ of the huminate of the invention was 2,700 mg/1000 ml.

| Contaminant | Action in contaminated water | | | |
|---|---|---|---|---|
| | Amount of contaminant | Quant. of huminate | Survival time in hours | $LC_{50}$ mg/1000 ml |
| Cadmium chloride | 1 mg/lt | 0 ppm | 0.2 | 0.5 |
| | | 20 ppm | 3 | 2.5 |
| Lead acetate | 5 mg/lt | 0 ppm | 0.5 | 2.5 |
| | | 20 ppm | 6 | 7.5 |
| Mercury 1-chloride | 3 mg/lt | 0 ppm | 0.5 | 0.5 |
| | | 20 ppm | 1.5 | 2.8 |
| Parathion | 4 mg/lt | 0 ppm | 0.2 | 0.5 |
| | | 20 ppm | 24 | 10.0 |
| Atrazine | 4 mg/lt | 0 ppm | 0.5 | 2.0 |
| | | 20 ppm | 4.5 | 10.0 | or teratogenicity of humins, it is not the molecular weight range of 300 to 1500 that is necessary for their activity but other criteria.

It has now been found that additional huminates of higher molecular weight, i.e. up to about 50,000 D, also possess the healing properties with very low toxicity and non-mutagenic and non-teratogenic properties. The common characteristic of these desired huminates is that their aqueous solutions show no Tyndall effect and do not fluoresce. Tests for these properties are carried out with aqueous solutions at a concentration wherein they still have about 50% transmission of the irradiated light.

The huminates may be simply produced by oxidation of polyvalent phenols in an aqueous alkaline medium at temperatures below 40° C. if the pH of the reaction medium is always more than 9.0 and the amount of oxidant is regulated so that the amount of the quinones corresponding to the polyvalent phenols is always less than 0.5% based on the polyvalent phenol used and then stopping the oxidation when the quinone concentration decreases despite the supply of oxidant. Preferably, the oxidation is halted when the quinone concentration falls below 0.5% by weight based on the polyvalent phenol.

Examples of suitable starting materials are all known polyvalent phenols such as pyrocatechol, resorcinol, hydroquinone, orcinol, gallic acid, protocatechuic acid, pyrogallol, 2-oxyhydroquinone, phloroglucinol or tetraoxybenzoles. The polyvalent phenols may be used in pure form or as mixtures thereof. The preferred starting material is hydroquinone.

Preferably, the polyvalent phenols are dissolved in aqueous alkaline solution and examples of suitable bases are alkali metal hydroxides or carbonates, ammonia and strong amines, preferably sodium hydroxide or potassium hydroxide for economical reasons. The amount of the base should be more than 1.6 times the stoichiometric amount necessary for phenolate formation of the polyvalent phenols to ensure neutralization of all the phenolic hydroxy groups. The reaction medium will then have a pH greater nine.

The alkalinity of the reaction solution may be greater but since the reaction medium has to be neutralized for processing, it is preferred for economical reasons not to use too highly an alkaline solution. It is preferred to keep the pH slightly greater than 9 and to add more base during the reaction to prevent a decreae in the pH value.

Obviously, the compounds used should be as pure as possible to avoid undesired secondary reactions, or respectively, the end products can be obtained without any further chemical processing which, too, would involve undesired chemical modifications of the end products and can be used in the reaction medium obtained. Generally it is sufficient to use as water, demineralized water of a conductivity of 6 to $10/\mu S/cm$ and a pH value in the range from 5 to 7, and as the alkali metal hydroxide either a "chemically pure" grade or of the purity per DAB of 9. As polyvalent phenol, likewise a "chemically pure" grade of a polyvalent phenol content of more than 98% should be used.

The oxidation of the polyvalent phenol can occur either electrochemically or plasmachemically, or respectively chemically by causing oxygen or an oxygen-containing gas mixture to pass over or through the reaction mixture. The electrochemical oxidation occurs in an electrochemical reaction, with the rate of oxidation being determined by setting the anodic voltage and the current density. The anodic voltage can be varied in the range from 4 to 16 volts and the current density in the range from 0.5 to 4 $A/cm^2$. The reaction time is then in the range of 1 to 3 days.

The plasmachemical oxidation occurs in an apparatus known per se for corona discharge with the oxidation rate being determined by setting the operating voltage and the field strength. The voltage may be varied in the range of 20 to 250 kv at frequencies of 16⅔ to 400 Hz, and the field strength from 80 kv/cm to 200 kv/cm. The reaction time is then in the range of 15 to 1000 minutes.

For chemical oxidation, the alkaline solution of the polyvalent phenolate is placed in a reaction vessel which prevents uncontrolled access of air, that is, in a closed reaction vessel, but which is provided with a device for letting gases in or through. While stirring, oxygen or an oxygen-containing gas mixture is passed in a continuous gas stream either over or through the reaction solution or is conducted onto the reaction solution under pressure, the temperature of the reaction mixture being in the range from 10° to 40° C., preferably from room temperature to 30° C.

As oxygen-containing gas mixture, air can be used which, however must first be conducted over an alkaline filter for adsorption of $CO_2$ and for the removal of dust particles. The chemical oxidation can occur also by reaction with mild oxidants such as hydrogen peroxide, its addition compounds, or persulfates.

During the oxidation reaction, the pH value of the reaction mixture and the content of quinone corresponding to the polyvalent phenol in the reaction mixture are monitored. As soon as one of he two parameters is fallen short of or exceeded, the reaction must be stopped. The oxidation reaction is controlled through the amounts of oxidant used, the term oxidant to be understood, depending on the process employed, as chemical reagent or as applied voltage and current stength.

As a rule, the reaction time is 10 to 15 days. The reaction is terminated, if despite additional supply of oxidant, the quinone content decreases, preferably when the quinone concentration has fallen to a value below 0.05%, referred to the polyvalent phenols used.

Thereafter, the reaction mixture is acidified in a manner known in itself to a pH value in the range from 4 to 5, and is processed by methods known in themselves, as e.g. ultra-centrifugation, ultrafiltration or electrophoresis. Thus, for example, the dark brown solution resulting from the chemical, plasmachemical or electrochemical oxidation reaction is adjusted to a pH in the range from 4 to 5, preferably 4.5 and possibly buffered. This is done either by addition of acid or by action of acid ion exchanger and/or subsequent addition of a corresponding buffer solution.

If the neutralized and buffered solution contains undesired suspended substances, these substances are removed by a separating process such as centrifuging $(10,000$ to $30,000 \times g)$. Although for many applications, this solution can be used directly, it should be purified and freed of undesired secondary products by purification processes known in themselves, such as preparative chromatography methods, ultrafiltration, ultra-centrifugation or electrodialysis, if the products are used as medicaments.

Thereafter, the brown solution can be concentrated to 3 to 5% huminate (to about 40% huminate) or dried by means of a suitable dryer to a residual moisture of 2%. By drying, a readily crumbling, crystalline, hygroscopic substance of a lustrous black color is obtained. The dilute as well as the concentrated solution and also the solid obtained are stable.

In stability tests, after 60 days of load cycles 66/4° C. in the 12/12 hour rhythm, no alteration of the parameters content, pH value, redox potential and microdialysis test beyond accidental fluctuations is observable. Toxicity tests show that the huminates are little toxic, but it was found that the huminates produced also have the same healing actions and detoxifying effects observed in the mentioned low-molecular weight humins.

The huminates of the invention are therefore suitable for all applications that are known of the natural or synthetic low-molecular weight humins. In particular, they are useful as wound medicaments, for the preparation of wound-healing products, for the production, of highly effective moor baths, nose medicines against pollen allergies, anti-dandruff shampoos, as well as agents for the treatment of fishes, particularly fish under stress. In addition, they are suitable for detoxification of water as well as of surfaces or solid objects contaminated with cholinesterase-inhibiting substances of the organophosphate type and/or with dermatotoxic substances of the dichlorodiethylsulfide type.

In the following examples, there are described several preferred embodiemnts to illustrate the invention. However, it is to be understood that the invention is not intended to be limited to the specific embodiments.

EXAMPLE 95 kg of potassium hydroxide (DAB 9 quality) were dissolved in 1,000 liters of demineralized water with a pH of 5 to 7 and a conductivity under 5 $\mu S/cm$ in an alkali-resistant vessel. After cooling the solution to below 40° C., 55 kg of hydroquinone 99% chemical purity) were added thereto over 45 minutes with cooling to ensure the temperature did not exceed 40° C. The pH adjusted itself to about 10. The vessel was closed and air purified of dust, carbon dioxide and other contaminants through an alkaline filter system was passed over the surface of the stirred mixture. The air stream was regulated so that the content of 1,4-benzoquinone was always less than 0.5% by weight following $LD_{50}$ values were obtained: based on the hydroquinone added. The reaction temperature was always below 40° C. and the pH was always above 9.

After 10 to 15 days, the hydroquinone content of the brown reaction solution dropped to below 2% and despite the further supply of air, the content of 1,4-benzoquinone fell to values below 0.05%. At this moment, the reactin was stopped and the supply of air was halted. The reaction mixture was adjusted to a pH value of 4.5 by addition of an acid ion exchanger which was separated by centrifuging. The acid solution was subjected to ultrafiltration, using a filtration device of 0.5/yum purity and the ultrafiltrate was concentrated under a weak vacuum to a huminate concentration of 40% by weight. The solution can still be handled easily and contained huminates with molecular weights in the range of 1,000 to 50,000. The solution did not show a Tyndall effect and contained no fluorescing components.

Toxicity

When test mice were injected with the 1% solution, the following $LD_{50}$ values were obtained:
1370 mg/kg subcutaneously 920 mg/kg intraperitoneally
840 mg/kg intraveinously

Stability

No changes were observable after storage for 6 months under exclusion of air at 23° C.

Healing effects

A culture of L cells (mouse fibroblasts) suspended after treatment with thrypsine was mixed with 50 ppm of huminate and the culture was incubated for 48 hours at 37° C., using a commercial culture medium. At the same time, a similar culture without huminates was incubated in the same manner as a control. Then, the number of living cells was determined in both cultures. In the culture mixed with huminate of the invention, the number of living cells was 30% higher than in the control culture.

Healing of wounds

On 2 groups of 10 hairless mice, superficial wounds affecting only the topmost epithelium layers were inflicted with a size of about 50 $mm^2$, using a microdermatome. In ten of these mice, the wound was wetted once with a 1% huminate solution and the other 10 mice remained untreated. During the observation period of 7 days, the following were observed: As compared with the untreated mice, the wound area decreased quicker in the treated test animals and the wound dried up earlier, the granulation set in earlier, and the wound became clean earlier. On the whole, healing was observable 2 to 3 days earlier than in the control animals.

Action in stressed fish

Groups of 50 fish of different species were placed after a transport into three different basins, each containing 70 liters and they were observed and compared for 7 days. The conditions of keeping and feeding were the same in each instance. Only the water, identical in principle, had been changed by additions: Basin a: no addition; Basin b: 20 ml (prescribed dose) of a commercial humic acid-containing prophylactic; and Basin c: 3 ml of a 2% aqueous solution of the huminate of the invention. After 2 days, an additional 2 ml of the 2% solution were added.

Activity as nose medicine

A test group of 10 persons suffering from allergic reactions caused by pollen, especially in the nose and eye region, used a 0.5% aqueous solution of the huminate of the example as a nose spray by spraying a dose of the solution into the nose when the hay fever symptoms appeared, using a conventional bottle as normally used for nose sprays. The discomforts diminished in all patients within minutes. Their noses became free, the sneeze irritation disappeared and the swelling up of the eyes was reduced. Undesirable side effects were not observed even after prolonged use of the product. Six of the test persons reported that after using the product for several days, the number of necessary applications was substantially reduced. On days of low pollen count, these patients were without discomfort even without the nose spray of the invention.

Action of the anti-dandruff product

To 100 ml portions of a commercial shampoo, there were added 50 ml of a 5% aqueous solution of the huminate of the above example. Various test persons suffering from dandruff used one of the dilute shampoos they had obtained twice with 5 ml each for their daily hair and scalp wash. The results were the same in all cases: After a period of application of about one week, the dandruff problem was no longer acute. Evem after using the shampoo for several weeks, no increase of sebaceous gland activities was observable on the scalp. In some cases, a reduction of the hair greasing was observed subjectively.

Various modifications of the compositions and method of the invention may be made without departing from the spirit or scope thereof and it is to be understood that the invention is intended to be limited only as defined in the appended claims.

What we claim is:

1. In a process for the production of physiologically active, non-toxic, non-teratogenic and non-mutagenic huminates by oxidation of polyvalent phenols in alkaline, aqueous medium at a reaction temperature under 40° C. and subsequent isolation, the improvement comprising the pH of the reaction medium is always over 9.0 during the oxidation and the supply of the oxidant is proportioned so that the content of the formed quinones corresponding to the polyvalent phenol is always less than 0.5% based on the polyvalent phenols used, and that the oxidation reaction is stopped when despite the supply of oxidant, the quinone concentration decreases, the aqueous solutions of the huminate show no Tyndall effect and do not fluoresce.

2. The process of claim 1 wherein the oxidation reaction is stopped when, despite the supply of oxidant, the quinone concentration has dropped below 0.05%, based on the polyvalent phenols used.

3. The process of claim 1 wherein hydroquinone is used as the polyvalent phenol.

4. Huminate produced by the process of claim 1.

5. A method of increasing wound healing comprising applying to a wound of a warm-blooded animal a wound healing amount of a huminate of claim 4.

* * * * *